United States Patent [19]

Dönges et al.

[11] Patent Number: 5,747,468
[45] Date of Patent: May 5, 1998

[54] CATIONIC UNSATURATED SACCHARIDES AND POLYMERS PREPARED THEREFROM, AND THEIR USE

[75] Inventors: Reinhard Dönges, Bad Soden; Rudolf Ehrler, Flörsheim, both of Germany

[73] Assignee: Hoechst Aktiengesellschaft, Frankfurt, Germany

[21] Appl. No.: 703,201

[22] Filed: Aug. 26, 1996

[30] Foreign Application Priority Data

Aug. 25, 1995 [DE] Germany .................. 195 31 264.3

[51] Int. Cl.$^6$ .................. A61K 31/70; A61K 7/06; C07H 5/06

[52] U.S. Cl. .................. 514/42; 424/70.28; 514/53; 514/54; 514/61; 514/844; 536/29.1; 536/123.1; 536/123.13

[58] Field of Search .................. 536/18.5, 29.1, 536/123.1, 123.13; 424/70.28; 514/844, 846, 847, 42, 53, 54, 61

[56] References Cited

U.S. PATENT DOCUMENTS

| | | | |
|---|---|---|---|
| 4,213,960 | 7/1980 | Grollier et al. | 424/47 |
| 4,328,337 | 5/1982 | Kawasaki et al. | 536/119 |
| 4,465,827 | 8/1984 | Kawasaki et al. | 536/18.6 |
| 4,710,374 | 12/1987 | Grollier et al. | 424/61 |
| 4,839,166 | 6/1989 | Grollier et al. | 424/71 |
| 5,277,899 | 1/1994 | McCall | 424/71 |

FOREIGN PATENT DOCUMENTS

| | | |
|---|---|---|
| 166089 | 1/1986 | European Pat. Off. |
| 0311799 | 4/1989 | European Pat. Off. |
| 2952507 | 7/1980 | Germany . |
| 06116341 | 4/1994 | Japan . |

OTHER PUBLICATIONS

Makromolekulare Chemie, Macromolecular Chemistry and Physics; pp. 517–528; J. Klein et al.; 1990.
Makromolekulare Chemie, Macromolecular Chemistry and Physics; pp. 1217–1232; J. Klein et al; 1987.
McGraw–Hill Dictionary of Chemical Terms, McGraw–Hill, Inc., p. 446, (1984).

*Primary Examiner*—John Kight
*Assistant Examiner*—Howard C. Lee
*Attorney, Agent, or Firm*—Connolly & Hutz

[57] ABSTRACT

Cationic unsaturated saccharides of the formula I $$R^5R^4C=CHR^3-CH_2-N^{\oplus}R^1R^2-CH_2-CHR^3=CR^4R^5 X^{\ominus} \quad (I)$$

in which $R^1$ is a deoxysaccharide radical having 1 to 20 monomer units, $R^2$ has the same meaning as $R^1$ or is $C_1$–$C_{20}$-alkyl, $C_2$–$C_{20}$-alkenyl, $C_1$–$C_4$-hydroxyalkyl, $C_1$–$C_4$-alkylphenyl or a polyoxyethylene, polyoxypropylene or polyethyleneimine group having in each case 1 to 10 ethylene oxide, propylene oxide or ethyleneimine units, $R^3$, $R^4$ and $R^5$ are hydrogen or methyl and X is a halogen, tosylate or allyl-sulfate ion.

These compounds are obtained by reaction of deoxyaminosaccharides with allyl compounds. Polymers which are built up from these compounds or comprise these compounds as monomer units are suitable as flocculating and thickening agents.

6 Claims, No Drawings

CATIONIC UNSATURATED SACCHARIDES AND POLYMERS PREPARED THEREFROM, AND THEIR USE

DESCRIPTION

Cationic unsaturated saccharides and polymers prepared therefrom, and their use

Cationic polymers have a broad spectrum of use. It ranges from cosmetic formulations, in particular for hair care, via ion exchangers to paper auxiliaries and waste water treatment.

Those polymers in which the monomer units are based on carbohydrates are particularly of special interest for uses in biological systems and for medical applications, for example as depot stores for medicaments. Nonionic monomer units based on carbohydrates are already described in several instances in the literature. Thus, deoxy-amino sugars can be converted with reactive vinyl components based on acrylates into the corresponding acrylamides, which in turn can be polymerized (Makromol. Chem. 191, 517–528 (1990) and Makromol. Chem. 188, 1217 (1987)). Other polymerizable carbohydrate monomers which are known are the vinyl β-D-glycosides (Chem. Ber. 85, 175 (1952)), peracylated 1-O-acryloyl sugars (DE 2 952 507), N-p-vinylbenzyl-gluconamides (Polym. J. 17, 567 (1985)) and glycosylethyl methacrylates (J. Appl. Polymer Science 52, 1759–1763 (1994)).

Only very little is known about monomers based on carbohydrates which are cationic in nature. EP 0 166 089 describes polymerizable monomers which are built up such that the reactive polymerizable unit is linked to a carbohydrate via a glycoside bond. These compounds have some disadvantages. On the one hand, their synthesis proceeds via several stages. In the synthesis of the precursor, the glycosidation with 3-chloro-1,2-propanediol, oligomeric glycosides are formed and excess chloropropanediol must be removed by distillation. Because of the glycosidic bond, the polymers have no stability in the acid pH range.

The object of the invention was therefore to provide novel cationic polymerizable monomers based on carbohydrates, which are easy to prepare in a high yield and purity and are stable both in the acid and in the alkaline pH range.

The invention relates to cationic unsaturated saccharides of the formula I

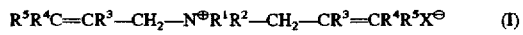

in which $R^1$ is a deoxysaccharide radical having 1 to 20 monomer units, $R^2$ has the same meaning as $R^1$ or is $C_1$–$C_{20}$-alkyl, preferably $C_1$–$C_4$-alkyl, $C_2$–$C_{20}$-alkenyl, preferably $C_2$–$C_4$-alkenyl, $C_1$–$C_4$-hydroxyalkyl, $C_1$–$C_4$-alkylphenyl or a polyoxyethylene, polyoxypropylene or polyethyleneimine group having in each case 1 to 10 ethylene oxide, propylene oxide or ethyleneimine units, $R^3$, $R^4$ and $R^5$ are hydrogen or methyl and X is a halogen, tosylate or allyl-sulfate ion.

These cationic unsaturated saccharides are prepared by reaction of deoxyaminosaccharides of the formula II

with allyl compounds of the formula (II)

in which $R^1$, $R^2$, $R^3$, $R^4$, $R^5$ and X have the abovementioned meanings.

The deoxyaminosaccharides of the formula 1111 are known per se (U.S. Pat. No. 2,830,983; EP-A-0,255,033; Makromol. Chem. 191, 517–528 (1990)). They are prepared by reductive amination of saccharides. Saccharides which can be employed are all the mono-, di- and oligosaccharides which contain an aldehyde or keto function (so-called reducing sugars) and have 1 to 20, preferably 1, saccharide units, such as, for example, glucose, maltose, fructose, isomaltulose, galactose, lactose and dextrins.

The term saccharides also includes those carbohydrates in which all or some of the hydroxyl groups are blocked in a known manner by protective groups, for example by acylation (acetyl groups), ketalization (isopropylidene or benzylidene groups) or etherification (methyl, hydroxyalkyl or carboxymethyl groups).

N-Alkyl-deoxyamino-monosaccharides, i.e. those compounds of the formula II in which $R^1$ is a deoxymonosaccharide and $R^2$ is $C_1$–$C_4$-alkyl, are preferred. Thus, for example, 1-(N-methylamino)-1-deoxysorbitol (N-methylglucamine) is obtained from methylamine and glucose, 1-(N-propylamino)-1-deoxymaltitol (N-methylglucamine) is obtained from propylamine and maltose, 1-(N-propylamino)-1-deoxymaltitol (N-methylmaltamine) is obtained from propylamine and maltose, or a mixture of 2-(methoxypropylamino)-2-deoxy-D-glucopyranosylmannitol and -sorbitol is obtained from methoxypropylamine and isomaltulose.

The compounds of the formula I are obtained in a quantitative yield by reaction of these deoxyaminosaccharides with 2.0 to 2.5 molar equivalents of an allyl compound of the formula III in the presence of one molar equivalent of a base, such as, for example, an alkali metal hydroxide, preferably NaOH. A possible allyl compound of the formula III is, above all, allyl chloride, but in addition also diallyl sulfate and allyl tosylate.

Suitable solvents for the reaction are water, water-soluble alcohols, such as methanol, ethanol or isopropanol, or ketones, such as acetone or methyl ethyl ketone, and also aprotic dipolar solvents, such as dimethyl sulfoxide, dimethylformamide, N-methylpyrrolidone or mixtures of these solvents. The preferred solvent is water.

A procedure is expediently followed in which a 20 to 70% strength, preferably 30 to 60% strength, solution of the deoxyaminosaccharide II is initially introduced into the desired solvent, and the allyl compound and the alkali metal hydroxide are then added dropwise at 40° to 100° C., but preferably at the boiling point of the allyl compound, such that a slightly alkaline pH of 8 to 10, but preferably 8.5 to 9.5, is present. The duration of the dropwise addition depends on the reaction temperature. Values of 1 hour to 5 hours are customary. Stirring is continued in a phase of the after-reaction, controlling the pH, until all the allyl compound has reacted. Typical times for the duration of the after-reaction are 1 hour to 10 hours, preferably 5 to 8 hours. Thereafter, the mixture is cooled and brought to pH 6.5 to 7.5 with a mineral acid, preferably hydrochloric acid. The solution thus obtained now comprises the compounds of the formula I in a ready-to-use form. However, the solution also comprises a molar amount of a salt which has formed in the neutralization during the reaction, as well as smaller amounts of the allyl alcohol corresponding to the allyl compound III. If these products are to be removed, the reaction solution is evaporated as far as possible in vacuo, low-boiling impurities and impurities which are volatile in steam being removed. A solvent which dissolves the ammonium compound, if necessary by heating, but leaves behind the salt to be removed as a sediment, is added to the residue. Solvents which have proved to be suitable are propanols and ethanol, and mixtures thereof. The solution is now filtered and the filtrate is evaporated again. The products according to the invention are thus obtained in an analytically and spectroscopically pure form, usually as hygroscopic, very viscous liquids. These can be diluted with water to give solutions which are easy to handle. Concentrations of 40 to 70% by weight are preferred. The basic nitrogen value of the product, determined by titration with perchloric acid standard solution in glacial acetic acid, can be used as evidence of the completeness of the reaction. It is less than 0.1%. In the $^1$H-NMR spectrum, the vinyl H atoms have absorptions between 5.5 and 6.2 ppm, and the $^{13}$C-NMR spectrum shows the absorptions of exactly 2 vinyl carbon atoms in the region around 130 ppm.

The products according to the invention thus obtained can be converted, either as solutions or in bulk, into high molecular weight products by homopolymerization, copolymerization or grafting copolymerization. The monomers of the formula I result in recurring units of the formula

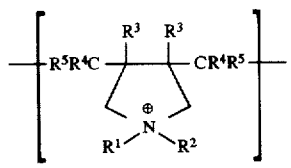

in this polymerization.

Suitable comonomers are all the polymerizable vinyl monomers, for example the derivatives of acrylic acid, styrenes, vinyl ethers, sulfonates, phosphonates, acetates and -acetamides, or other diallylammonium compounds. Monomers which are water-soluble are particularly suitable for solution copolymerization. The grafting copolymerization can be carried out on all the polymeric compounds which are capable of forming free radicals. However, polymeric carbohydrates and derivatives thereof are particularly suitable as the grafting base.

The procedures for the preparation of such high molecular weight compounds are adequately known from the prior art, for example polymerization in bulk, solution polymerization, suspension polymerization and emulsion polymerization. Free radical initiators which can be used are, for example, peroxides, such as hydrogen peroxide, di-tert-butyl peroxide, dibenzoyl peroxide and dilauroyl peroxide, azo compounds, such as 2,2'-azobis-(isobutyronitrile) and azobis(2-amidinopropane) dihydrochloride, or alkali metal and ammonium persulfates, redox initiator systems or UV, beta or gamma radiation.

A solution polymerization in water is to be preferred, water-soluble products, such as alkali metal or ammonium persulfates or quaternary azoamidine salts, such as, for example, azobis(2-amidinopropane) dihydrochloride expediently being employed as the free radical initiators. Working up of the polymers depends on the nature of the polymers present. Thus, homopolymers can be isolated by precipitation from a suitable solvent, but they can also be employed directly as finished solutions, for example as flocculating agents. Copolymers and graft copolymers are purified by reprecipitation from a suitable solvent or solvent mixture. Acetone, isopropanol, ethanol and methanol and mixtures thereof with water have proved to be suitable precipitating agents. The copolymers are characterized in elemental analysis by combustion analysis and by potentiometric chloride titration.

The homo-, co- or graft polymers thus obtained are used as flocculating agents for acid waste waters. Because of their particular skin-friendliness, they are furthermore also suitable as thickening agents in cosmetics.

EXAMPLES

1. Preparation of Diallyimethylglucammonium Chloride 1340 g of a 41% strength aqueous methylglucamine solution (corresponding to 2.9 mol of methylglucamine) are initially introduced into a 3 l multi-necked flask with a reflux condenser, stirrer, 2 dropping funnels, pH electrode and nitrogen inlet. 475 g (6.2 mol) of 3-chloro-1-propene (allyl chloride), are initially introduced into the first dropping funnel and a solution of 116 g (2.9 mol) of sodium hydroxide in 200 g of water is initially introduced into the other. At the start of the reaction, the pH of the solution is 12.0. The mixture is heated to 50° C. and 3-chloro-1-propene is added dropwise. After 2 hours, about half has been added dropwise and the pH has fallen to 9. The remaining 3-chloro-1-propene is now further added dropwise in the course of 3 hours, a pH of 9 to 9.5 being maintained simultaneously by addition of the sodium hydroxide solution from the second dropping funnel. Stirring is continued for a further 8 hours at a pH of 9.5 and a temperature of 50° C. The mixture is cooled to room temperature and brought to a pH of 7 with about 9 g of 37% strength hydrochloric acid. For working up, the solution is concentrated on a rotary evaporator, isopropanol being added several times for azeotropic removal of the water. The residue is dissolved in 2 l of isopropanol, which is heated to about 60° C., and sodium chloride is filtered off from the residue. The residue is rinsed twice more with hot isopropanol, dried and weighed (156 g of sodium chloride). The collected isopropanol solutions are evaporated to dryness on a rotary evaporator. Residual isopropanol is carried off azeotropically with water. The product is obtained as a colorless, highly viscous resin.

The chloride content (potentiometric) is 11.1% (theory 11.4%) and the residual basic nitrogen is 0.04%. The product is diluted with 1500 g of water to give a slightly viscous 63% strength solution. In the $^1$H-NMR spectrum (300 MHz in DMSO-d$_6$), in addition to the protons of the methyl group and of the carbohydrate moiety, the signals issued by the terminal vinyl protons at 5.50 to 5.75 ppm and the internal vinyl proton at 6.00 to 6.20 ppm are also to be detected, in each case with the typical splitting pattern and a vinyl/methyl intensity ratio of 2:1. In the $^{13}$C-NMR spectrum (75.4 MHz in DMSO-d$_6$), 10 different signals for carbon atoms are to be detected: 48.4 ppm, 63.7 ppm, 63.8 ppm, 64.6 ppm, 67.3 ppm, 70.4 ppm, 71.0 ppm, 71.9 ppm, 126.1 ppm and 128.6 ppm. In addition to these signals, no further signals are to be detected, apart from the solvent.

2. Preparation of Diallylmethyllactammonium Chloride 181 g of a 36% strength aqueous methyllactamine solution (prepared by reductive amination of lactose with methylamine) are initially introduced into a 500 ml multi-necked flask with a reflux condenser, precision glass stirrer, 2 dropping funnels, pH electrode and nitrogen inlet. 40.5 g of 3-chloro-1-propene (allyl chloride) are initially introduced into one dropping funnel and a solution of 10 g of sodium hydroxide in 25 g of water is initially introduced into the other. At the start of the reaction, the 10 pH of the solution is 11.8. The mixture is heated to 50° C. and 3-chloro-1-propene is added dropwise. After 2 hours, about half has been added dropwise and the pH has fallen to 9. The remaining 3-chloro-1-propene is now further added dropwise in the course of 3 hours, a pH of 9 to 9.5 being maintained simultaneously by means of the sodium hydroxide solution. Stirring is continued for a further 8 hours at a pH of 9.5 and a temperature of 50° C. The mixture is cooled to room temperature and brought to a pH of 7 with 37% strength hydrochloric acid. For working up, the solution is concentrated on a rotary evaporator, isopropanol being added several times for azeotropic removal of the water. The residue is dissolved in 1 l of boiling ethanol and the solution is filtered. After drying, 14.3 g of sodium chloride remain. The ethanolic solution is evaporated to dryness on a rotary evaporator. Residual ethanol is carried off azeotropically with water. The product is obtained as a colorless, highly viscous resin. The product still contains 0.06% of basic nitrogen. It is diluted with 160 g of water to give a slightly viscous, 52% strength solution.

3. Homopolymerization of Diallylmethylglucammonium Chloride 170 g of the 63% strength solution of diallylmethylglucammonium chloride from Example 1 are initially introduced into a three-necked flask with a nitrogen inlet and septum. The flask is evacuated and aerated with nitrogen several times. The solution is heated up to 80° C. under an inert atmosphere and a solution of 0.80 g of ammonium persulfate in 5 ml of degassed water is injected in via the septum. After 24, 48 and 72 hours, in each case 0.80 g of ammonium persulfate in 5 ml of water is added again in this manner. A highly viscous polymer solution is obtained.

4. Copolymerization of Acrylamide and Methyldiallylglucammonium Chloride 56.6 g of acrylamide and 99.3 g of methyldiallylglucammonium chloride solution (63% strength by weight) from Example 1 are initially introduced into 150 g of degassed water in an apparatus as described in Example 3. The mixture is heated up to 60° C. and a solution of 1.0 g of 2,2'-azobis(2-amidinopropane) dihydrochloride in 3 ml of water is slowly added over the course of 30 minutes via the septum. The mixture is subsequently stirred at 80° C for 5 hours to give a clear viscous solution. This is poured into 2 l of methanol, with vigorous stirring (Ultra Turrax), the polymer precipitating. This is stirred up twice more with 1 l of methanol and filtered off with suction. The product is dried at 70° C. 92 g of a colorless powder having a chloride content of 4.01% and a viscosity of 333 mPas as a 10% strength by weight formulation in water, measured with a Höppler viscometer, are obtained.

5. Copolymerization of Acrylamide and Methyldiallylglucammonium Chloride 113.8 g of acrylamide and 99.3 g of methyldiallylglucammonium chloride solution (63% by weight) from Example 1 are initially introduced into 450 g of degassed water in an apparatus as described in Example 3. The mixture is heated up to 60° C. and a solution of 2.0 g of 2,2'-azobis(2-amidinopropane) dihydrochloride in 6 ml of water are slowly added over the course of 30 minutes via the septum. The mixture is subsequently stirred at 80° C. for 5 hours to give a clear viscous solution. This is poured into 2.5 l of methanol, with vigorous stirring (Ultra Turrax), the polymer precipitating. This is stirred up twice more with 1 l of methanol and filtered off with suction. The product is dried at 70° C. 150 g of a colorless powder having a chloride content of 2.40% and a viscosity of 2210 mPas as a 10% strength by weight formulation in water, measured with a Höppler viscometer, are obtained.

6. Copolymerization of Acrylic Acid and Methyldiallylglucammonium Chloride 14.4 g of acrylic acid and 99.3 g of methyldiallylglucammonium chloride solution (63% strength by weight) from Example 1 are initially introduced into 100 g of degassed water in an apparatus as described in Example 3. The mixture is heated up to 60° C. and a solution of 0.5 g of 2,2'-azobis(2-amidinopropane) dihydrochloride in 2 ml of water is slowly added over the course of 2 hours via the septum. The mixture is subsequently stirred at 80° C. for 2 hours to give a clear, only slightly viscous solution. This is brought to a pH of 10.5 with 30% strength sodium hydroxide solution, 500 ml of isopropanol are added and the mixture is evaporated in vacuo. The residue is poured into 2.5 l of methanol, with vigorous stirring (Ultra Turrax), the polymer precipitating. This is stirred up twice more with 2 l of methanol and filtered off with suction. The product is dried at 70° C. 41.1 g of a colorless powder having a chloride content of <0.1%, a nitrogen content of 2.7% and a viscosity of 970 mPas as a 10% strength by weight formulation in water, measured with a Höppler viscometer, are obtained.

7. Copolymerization of 2-Acrylamido-2-Methylpropanesulfonic Acid and Methyldiallylglucammonium Chloride 82 g of 2-acrylamido-2-methylpropanesulfonic acid and 99.3 g of methyldiallylglucammonium chloride solution (63% strength by weight) from Example 1 are initially introduced into 100 g of degassed water in an apparatus as described in Example 3. The mixture is heated up to 60° C. and a solution of 0.5 g of 2,2'-azobis(2-amidinopropane) dihydrochloride in 2 ml of water is added in a period of 15 minutes via the septum. The mixture is subsequently stirred at 80° C. for 5 hours to give a clear viscous solution. This is brought to a pH of 7 with 30% strength sodium hydroxide solution, 500 ml of isopropanol are added and the mixture is evaporated in vacuo. The residue is poured into 2.5 l of ethanol, with vigorous stirring (Ultra Turrax), the polymer precipitating. This is stirred up twice more with 2 l of ethanol and filtered off with suction. The product is dried at 70° C. 108 g of a colorless powder having a chloride content of 0.4%, a nitrogen content of 5.5% and a sulfur content of 9.4% are obtained.

8. Grafting Copolymerization of Methyldiallylglucammonium Chloride onto Carboxymethylicellulose 96.8 g of carboxymethylcellulose CB 30000 (Tylosel®, viscosity about 30000 mPas as a 2% strength formulation in water, DS=0.68), 350 g of dimethoxyethane and 104 g of diallylmethylglucammonium chloride monomer solution (63% strength, from Example 1) are initially introduced into a 2 l stirred reactor with a reflux condenser, line for passing over nitrogen and internal thermometer at room temperature. The mixture is heated up to 50° C. and degassed while passing through a gentle stream of nitrogen and stirring slowly. 2.0 g of 2,2'-azobis(2-amidinopropane) dihydrochloride, finely powdered, are then added and the mixture is stirred at room temperature for 1 hour. It is heated up to 70° C. and stirred slowly at 70° C. for 16 hours. The product is filtered off with suction, washed out 6 times with 60% strength aqueous isopropanol and twice with acetone and dried at 70°C. 101 g of a colorless powder having a sodium content of 5.22%, corresponding to a degree of substitution with respect to carboxylate of 0.68 mol/anhydroglucose unit, and a nitrogen content of 0.8%, corresponding to an average degree of grafting of 0.17 mol/anhydroglucose unit, are obtained. The viscosity of a 2% strength solution of the grafted polymer is 3490 mPas, measured on a Höppler viscometer.

9. Grafting Copolymerization of Methyldiallylglucoammonium Chloride onto Hydroxyethylcellulose 100 g of hydroxyethylcellulose H10000 (Tylosel®, viscosity about 10000 mpas as a 2% strength formulation in water, MS=2.40), 450 g of cyclohexane and 85 g of diallylmethylglucammonium chloride monomer solution (63% strength, from Example 1) and 30 g of dibenzoyl peroxide are initially introduced into a 2 l stirred autoclave at room temperature. The mixture is rendered inert and then heated at 90° C. for 6 hours, while stirring. After cooling, the product is filtered off with suction, washed out 6 times with 80% strength aqueous isopropanol and twice with acetone and dried at 70° C. 84 g of a colorless powder having a nitrogen content of 0.6%, corresponding to an average degree of grafting of 0.13 mol/anhydroglucose unit, are obtained. The viscosity of a 2% strength solution of the grafted polymer is 620 mpas, measured on a Höppler viscometer.

We claim:

1. A deoxyaminosaccharide compound represented by formula I $$R^5R^4C=CR^3-CH_2-N^{\oplus}R^1R^2-CH_2-CR^3=CR^4R^5 X^{\ominus} \qquad (I)$$

in which $R^1$ is a deoxysaccharide radical having 1 to 20 monomer units, $R^2$ has the same meaning as $R^1$ or is $C_1-C_{20}$-alkenyl, $C_1-C_4$-hydroxyalkyl, $C_1-C_4$-alkylphenyl or a polyoxyethylene, polyoxypropylene or polyethyleneimine group having in each case 1 to 10 ethylene oxide, propylene oxide or ethyleneimine units, $R^3$, $R^4$ and $R^5$ are hydrogen or methyl and X is a halogen, tosylate or allyl-sulfate ion.

2. The deoxyaminosaccharide compound of claim 1, wherein $R^1$ is a deoxymonosaccharide radical $R^2$ is $C_1-C_4$-alkyl or $C_1-C_4$-hydroxyalkyl, $R^3$, $R^4$ and $R^5$ are each a hydrogen atom and X is a chloride ion.

3. The deoxyaminosaccharide compound of claim 1, wherein $R^1$ is a 1-deoxyglucityl, 1-deoxygalactityl, 1-deoxylactityl or 1-deoxymaltityl radical.

4. A process for preparing the deoxyaminosaccharide compound of claim 1, which comprises reacting a deoxyaminosaccharide of the formula II $$R^1R^2NH \qquad (II)$$

with an allyl compound of the formula III $$XCH-CR^3=CR^4R^5 \qquad (III)$$

in which $R^1$, $R^2$, $R_3$, $R_4$, $R^5$ and X have the meanings given in claim 1.

5. A homo-, co- or graft polymer made from the deoxyaminosaccharide compound of claim 1.

6. A method of thickening/flocculating a cosmetic composition which comprises adding a thickening/flocculating effective amount of the homo-, co- or graft polymer of claim 5.

* * * * *